United States Patent [19]

Schricker

[11] Patent Number: 4,670,248

[45] Date of Patent: Jun. 2, 1987

[54] OLIVINE BOLUS

[75] Inventor: Brian R. Schricker, Terre Haute, Ind.

[73] Assignee: International Minerals & Chemical Corp., Terre Haute, Ind.

[21] Appl. No.: 765,850

[22] Filed: Aug. 15, 1985

[51] Int. Cl.[4] .......................... A61K 9/32; A61K 9/24
[52] U.S. Cl. ..................................... 424/19; 424/155; 604/890; 604/892
[58] Field of Search ........................ 424/14, 15, 19, 22, 424/155; 604/890, 892

[56] References Cited

U.S. PATENT DOCUMENTS

| | | | |
|---|---|---|---|
| 3,056,724 | 10/1962 | Marston | 424/22 |
| 3,432,593 | 3/1969 | Shepard | 424/22 |
| 3,507,952 | 4/1970 | Rednick et al. | 424/22 |
| 3,577,513 | 5/1971 | Roebuck et al. | 424/22 |
| 3,728,445 | 4/1973 | Bardani | 424/22 |
| 4,104,370 | 8/1978 | Bloch | 424/19 |
| 4,163,777 | 8/1979 | Mitra | 424/155 |
| 4,181,709 | 1/1980 | Dannelly | 424/22 |
| 4,199,560 | 4/1980 | Gyarmati et al. | 424/155 |
| 4,293,539 | 10/1981 | Ludwig et al. | 424/22 |
| 4,331,652 | 5/1982 | Ludwig et al. | 424/22 |
| 4,333,919 | 6/1982 | Kleber et al. | 424/15 |
| 4,447,254 | 5/1984 | Hughes et al. | 424/14 |
| 4,473,545 | 9/1984 | Drake et al. | 424/22 |

Primary Examiner—Ronald W. Griffin
Attorney, Agent, or Firm—Wendell R. Guffey; George R. Repper; Thomas L. Farquer

[57] ABSTRACT

The present invention relates to a bolus adapted to be orally administered to ruminants. The bolus contains a mixture of a magnesium silicate, a binder, and a rumen-soluble material. The bolus of the present invention provides for the controlled release of supplemental magnesium as a means of preventing and combatting the disease known as hypomaganesemia. Optionally, the bolus of the present invention can serve as a carrier for various biologically active substances.

18 Claims, No Drawings

OLIVINE BOLUS

BACKGROUND OF THE INVENTION

It is often desirable and sometimes even necessary that various biologically active substances be given to ruminants in order to supplement their diet. Generally, these biologically active substances are mixed with their feed in order to provide the biologically active substances to the ruminant on a daily basis. Unfortunately, it is inconvenient to supplement the feed of various ruminants since they graze for long periods of time. Therefore, it is desirable to provide such ruminants with a daily supplement which can be released in the gastrointestinal tract over a prolonged period of time.

A variety of sustained release pellets or boluses have been disclosed in the art which provide for the release of a beneficial agent such as a nutrient or medicament. For example, U.S. Pat. No. 3,507,952 discloses a sustained release bolus for animal husbandry. These sustained dosage boluses remain in the rumeno-reticular sac of an animal over an extended period of time wherein the therapeutically active substance has a predicable and controlled release pattern. These compositions generally comprise a dense filler, a therapeutically active substance and a lubricant.

U.S. Pat. No. 3,577,513 relates to a pellet for ruminants containing magnesium or magnesium alloy and iron particles. This patent teaches that in order for the pellets, once introduced into the rumeno-reticular sac, to remain there for a considerable period of time it is necessary that the pellet be of specific gravity not less than 2.2.

While the above delayed-release or extended release tablets or capsules have been described as being suitable, most of these suffer from difficulty in manufacture and limitations on the amount of nutrients since tablets may require high levels of carriers. Therefore, there exist a need for a bolus which can be easily manufactured and is used for supplying the animals with a biologically active substance over prolonged periods of time and whereby the ratio of the components, directly control the release time of the biologically active substance.

SUMMARY OF THE INVENTION

The present invention relates to a bolus for administration to ruminants over an extended period of time of various biologically active substances. The bolus contains a mixture of a magnesium silicate, a rumen-soluble material and a binder. These boluses provide supplemental magnesium to the ruminant as an effective means of reducing problems with hypomaganesemia. In another embodiment, the magnesium silicate containing bolus may serve as a carrier for various other biologically active substances.

DETAILED DESCRIPTION OF THE PREFERRED EMBODIMENT

The bolus of the present invention provides magnesium to a ruminant as a means to reduce or prevent a disease known as hypomaganesemia. Hypomaganesemia is a metabolic disorder frequently associated with ruminants grazing cool season grasses. While this nutritional disorder has been studied extensively, the exact cause or combination of caustive factors is uncertain. Providing supplemental magnesium to ruminants has provided an effective means of reducing problems with this disorder. In most instances, providing up to 30 g of magnesium per head per day is recommended to meet the magnesium requirements of beef cattle. The requirement can be met through a combination of magnesium from feed and supplements. Conventionally, magnesium oxide is mixed into a supplemental feed to be fed daily. Unfortunately, many of the cattle are not available for daily supplemental feedings in view of their grazing nature. This invention is therefore, directed to such cattle as well as other ruminants by providing a magnesium containing bolus and a means to control the release rate of magnesium over an extended period of time.

The present invention comprises a mixture of a magnesium silicate, a rumen-soluble material and a binder. Examples of magnesium silicates which can be used in the present invention include olivine, serpentine, dunite and peridot, with olivine being preferred. Olivine is a natural magnesium-iron silicate, found in igneous and metamorphic rocks, meteorites and blast furnace slags. Olivine is commonly used in refractories and cements. Surprisingly, magnesium silicates can be used in a bolus for the purposes of providing supplemental magnesium to a ruminant. While the amount of the magneisum silicate can vary, generally it is in amounts of from about 50 to about 95 weight percent of the total weight of the bolus. Preferably, the magnesium silicate is from about 70 to about 85 weight percent.

Another ingredient in the bolus for the present invention is a rumen-soluble material. The rumen-soluble material enhances the rate of magnesium release in the aqueous environment of the rumen. By varying the ratio of the water-soluble material with the magnesium silicate, which is substantially insoluble in the conditions of the rumen, one can control the release rate of the magnesium and any additional biologically active ingredients contained in the bolus. Examples of rumen-soluble materials include starches, urea, biuret, and sugars such as lactose, fructose, sucrose, dextrose or the like. In addition to the above, other materials include calcium lactate, calcium glucose, calcium glycerophosphate, calcium formate, calcium citrate, calcium ascorbate, calcium acetate, calcium phosphates, calcium chloride, calcium oxide, calcium carbonate, calcium sulfate and calcium hydroxide. Instead of calcium being the cation in the above materials, the cation may be sodium, magnesium, potassium, magnanese, copper and zinc. Another group of rumen-soluble materials include ammonium compounds such as ammonium lactate, ammonium chloride, ammonium sodium phosphate, ammonium ferric citrate, ammonium cupric chloride, ammonium phosphate, ammonium sulfate and polyammonium phosphates. Preferably, the rumen-soluble material is urea. While the weight percent of the rumen-soluble material may vary, generally, the soluble material is present in amounts of from about 1 to about 50 weight percent of the total weight of the bolus. Preferably, the rumen-soluble material is from about 10 to about 30 weight percent.

In order to formulate the boluses of the present invention, various binders are used. Such binders include sodium bentonite, ethyl cellulose, stearic acid, calcium stearate, adipic acid, fumaric cid, polyethylene glycol, deacetylated chitlon and cellulose acetate. Generally, the binder is present in amounts of from about 0.5 to about 10 weight percent of the total weight of the bolus.

Preferably, the binder is present in amounts of from 2 to 3 weight percent.

Lubricants may be added to the bolus to assist in the ease of manufacture. Examples of such lubricants include those common tablet water insoluble lubricants such as, for example, magnesium stearate, sodium stearate, calcium stearate, powdered stearate acid, talc, paraffin, cocoa butter, graphite, lycopodium, boric acid, sodium oleate, sodium benzoate, sodium acetate, sodium lauryl sulfate, magnesium lauryl sulfate, or combinations thereof. Preferably, the lubricant is a fatty acid derivative such as the stearates, including magnesium stearate, sodium stearate, and calcium stearate. While the amount of lubricant may vary, the lubricant is generally present in amounts of from about 0.5 to about 10 percent by weight of the total weight of the bolus. Preferably, the lubricant is present in amounts of from about 1 to about 5 weight percent.

While the present invention is useful for providing a daily supplemental amount of magnesium over an extended period of time, the bolus of the present invention may be used as a carrier for other biologically active substances. Examples of such substances include additional nutritional trace elements aside from magnesium, anti-bloat agents, sedatives, tranquilizers, anti-convulsants, muscle relaxants, antipyretics, anti-inflammatories, analgesics, antimicrobials, steroids, diuretics, neoplastics, hypoglycemics, amino acids, vitamins, enzymes, bacterial cultures, antibiotics and anthelmentics.

Examples of such trace elements which may be administered with the bolus of the present invention include cobalt, nickel, copper, molybdenum, chromium, iron, iodine, zinc, selenium and manganese.

Polyether ionophore antibiotics, which promote growth and enhance feed utilization by the ruminant, can be intermixed with the olivine and rumen-soluble material. Ionophores are generally provided to the ruminant during a "fattening out" period of up three to six months. Examples of such polyether ionophore antibiotics growth hormones that can be used in the present invention include monensn, nigericin, salinomycin, narasin, grisorixan, lonomycin, laidomycin, mutalomycin, alborixin, lasalocid, lysocellin, ionomycin, aabomycin, disnerycin, duamycin or mixtures thereof. It will be appreciated that the salts and esters of such compounds can also be used.

Other antibiotics which can be incorporated in the bolus of the present invention provide an effective level of the antibiotic over extended periods to the tissues of the ruminant during which infection is expected. Examples of such antibiotics include penicillin, chlortetracycline, tetra-cycline, oxytetra-cyline and the like.

Anti-bloat agents may also be incorporated in the bolus of the present invention to protect the animal over a period of time when bloat is normally a problem with the ruminant. Examples of such conventional anti-bloating agents include silicones such as methyl-silicones, or acetbutylate or polyoxyethylene derivatives of ricinoleic acid.

In addition to the above, various insecticides which are suitable for injestion can be incorporated in the bolus of the present invention. Through the systematic release of such insecticides, various parasites such as the warble fly larvae, can be combatted over an extended period of time.

While the shape of the bolus may vary, such boluses are generally cylindrical, spherical, spheroidal or any other shape or form appropriately rounded and preferably devoid of sharp edges and protuberances. As can be appreciated by one skilled in the art, the shape of the bolus should be such that injury to the animal during administration and logdement in the rumen or the reticulum is avoided.

While the ratio of the rumen-soluble material and magnesium silicate controls the release rate of the magnesium and any optional biologically active substances incorporated therein, the bolus should have a density sufficient to withstand the harsh conditions of the rumen-reticulum during retention of the bolus in the rumen-reticulum. If the density of the bolus is not sufficient such that the bolus tends to float on the rumen particulate matter, the bolus may be prematurely shed by the ruminants prior to release of the biologically active ingredient. Magnesium silicate boluses which lodge in the rumen-reticulum of the animal must have a density greater than water, i.e., 1 g/cc. On the other hand, if the specific density of the bolus is too high, it is possible that the magnesium and/or additional biologically active substance will not be released. Preferably, the density is from about 1.3 to 3.0 with a range of from about 1.5 to about 2.0 being particularly preferred.

The following examples are provided in order to illustrate the present invention and as appreciated by one skilled in the art, are not intended to be limiting to the scope of the present invention.

EXAMPLE

Various boluses were produced for illustrating the present invention. The composition of each preparation is listed below in Table 1. The general procedure for their production was to mix the weighed components, size the material through a stainless steel screen, hand-fill the die, precompress the material by hand, top up the die cavity and compress.

The rate of magnesium released from a preparation was determined by placing three weighed tablets in a nylon bag. The tablets were then inserted in the rumen of a fistulated steer. The fistulated animal received a high-grain maintenance ration. Weight reduction and magnesium loss from the tablets for a given period of time were used to determine rate of release. Magnesium determinations were made before and after the tablets were exposed to the rumen environment. After exposure to the rumen, the tablets were rinsed in water, dried at 100° C., and allowed to equilibrate to the atmosphere before being weighed. The tablets were wet ashed using $HNO_3/H_2O_2$ and the magnesium determined using atomic absorption spectrophotometry. The weight and magnesium loss of the various boluses is listed below in Table 2.

TABLE 1

| Example No. | Ingredient | Weight (%) | Total Weight (g) | Length (in) | Density (9/cc) | Hardness (kg/sq inch) |
|---|---|---|---|---|---|---|
| 1 | Olivine | 77.75 | 7.57 ± 0.05 | 0.461 ± 0.004 | 1.88 | 28.57 ± 1.90 |
|   | Urea | 19.44 | | | | |
|   | Ethylcellulose | 2.33 | | | | |
|   | Magnesium Stearate | .49 | | | | |

TABLE 1-continued

| Example No. | Ingredient | Weight (%) | Total Weight (g) | Length (in) | Density (g/cc) | Hardness (kg/sq inch) |
|---|---|---|---|---|---|---|
| 2 | Olivine | 77.75 | 7.48 ± 0.14 | 0.445 ± 0.003 | 1.60 | 20.30 ± 2.29 |
| | Starch | 19.44 | | | | |
| | Ethylcellulose | 2.33 | | | | |
| | Magnesium Stearate | .49 | | | | |
| 3 (Control) | Olivine | 97.18 | 8.12 ± 0.09 | 0.477 ± 0.004 | 2.57 | 20.06 ± 1.57 |
| | Ethylcellulose | 2.33 | | | | |
| | Magnesium Stearate | 0.49 | | | | |
| 4 (Control) | Magnesium Oxide | 76.19 | 5.68 ± 0.04 | 0.413 ± 0.007 | 1.45 | 13.76 ± 1.20 |
| | Starch | 19.05 | | | | |
| | Magnesium Stearate | 4.76 | | | | |

TABLE 2

Weight and Magnesium Loss of Bolus Exposed to the Rumen

| Example No. | Time in Rumen (Days) | % Weight Loss (−) Gain (+) | % Mg Loss (−) |
|---|---|---|---|
| 1 | 4 | −42 | −21 |
| 1 | 8 | −73 | −64 |
| 1 | 10 | −47 | −32 |
| 1 | 12 | −80 | −76 |
| 2 | 10 | −45 | −39 |
| 3 (Control) | 7 | −5 | −7 |
| 3 (Control) | 14 | −6 | −6 |
| 4 (Control) | 10 | +25 | −6 |

Examples 1 and 2 indicate that the bolus of the present invention loses both appreciable quantities of magnesium as well as an overall weight loss in a rumen environment. These results demonstrate the feasibility of controlling magnesium release from a ruminal bolus due to manipulation of the relative amounts of rumen-soluble to poorly soluble magnesium silicate (olivine) material. Unlike Examples 1 and 2, the controls do not demonstrate significant weight loss or a high percent of magnesium loss in the rumen environment. Therefore, the above examples confirm that the rumen-soluble material, such as urea or starch enhance the rate of magensium release in the bolus of the present invention. The above data also demonstrates the continued and extended release of magnesium in the environment of a rumen bolus. Therefore, by varying the various mixtures of rumen-soluble material and magnesium silicate one can effectly manipulate the release rate of magnesium from the bolus of the present invention.

What is claimed is:

1. A controlled release bolus for administering supplemental magnesium to ruminants over an extended period, comprising:
   from about 50 to about 95 weight percent of a magnesium silicate selected from the group consisting of olivine serpentine, dunite and peridot,
   from about 1 to about 50 weight percent of a rumen-soluble material selected from the group consisting of urea ammonium lactate, ammonium chloride, ammonium sodium phosphate, ammonium ferric citrate, ammonium cupric chloride, ammonium phosphate, ammonium sulfate, polyammonium phosphate, buiret, starch, glucose, fructose, lactose, galactose, calcium lactate, calcium glucose, sodium lactate, magnesium lactate, magnesium glucose, cupric glucose, cupric lactate, zinc glucose, and zinc lactate; and
   from about 0.5 to about 10 weight percent of a binder.
2. The bolus of claim 1, wherein said magnesium silicate is olivine.
3. The bolus of claim 1, additionally containing a lubricant.
4. The bolus of claim 1, additionally containing further biological substances.
5. The bolus of claim 1, wherein said binder is selected from the group consisting of sodium bentonite, ethyl cellulose, stearic acid, calcium stearate, adipic acid, fumaric acid, polyethylene glycol, deacetylated chitlon and cellulose acetate.
6. The bolus of claim 3, wherein said lubricant is selected from the group consisting of magnesium stearate, sodium stearate, powdered stearic acid, talc, paraffin, cocoa butter, graphite, lycopodium or combinations thereof.
7. The bolus of claim 4, wherein said biological active substance is selected from the group consisting of nutritional trace elements, anti-bloat agents, sedatives, tranquilizers, anti-convulsants, muscle relaxants, antipyretics, anti-inflammatories, analgesics, antimicrobials, steroids, diuretics, neoplastics, hypoglycemics, amino acids, vitamins, ezymes, bacterial cultures, antibiotics and anthelmentics.
8. The bolus of claim 6, wherein said rumen-soluble material is urea.
9. The bolus of claim 7, wherein said trace element is selected from the group consisting of cobalt, nickel, copper, molybdenum, chromium, iron, iodine, zinc, selenium and manganese.
10. The bolus of claim 7, wherein said anti-bloat agent is selected from the group consisting of methylsilicones, acetbutdylate and polyoxyethylene derivatives of ricinoleic acid.
11. The bolus of claim 7, wherein said antibiotic is selected from the group consisting of penicillin, chlorotetrocycline, tetra-cycline and oxytetra-cyline.
12. The bolus of claim 7, wherein said antibiotic is a polyether ionophore antibiotic that is selected from the group consisting of monensn, nigericin, salinomycin, narasin, grisorixan, lonomycin, laidomycin, mutalomycin, alborixin, lasalocid, lysocellin, ionomycin, aabomycin, disnerycin, duamycin or mixtures thereof.
13. A controlled release bolus for administering supplemental magnesium to ruminants over an extended period, comprising:
   from about 50 to about 95 weight percent of a magnesium silicate selected from the group consisting of olivine, serpentine, dunite, and peridot;
   from about 1 to about 50 weight percent of a rumen-soluble material selected from the group consisting of urea and starch; and
   from about 0.5 to about 10 weight percent of a binder.
14. The bolus of claim 13, wherein said binder is selected from the group consisting of sodium bentonite, ethyl cellulose, stearic acid, calcium stearate, adipic acid, fumaric acid, polyethylene glycol, deacetylated chitlon and cellulose acetate.

15. The bolus of claim 13, additionally containing a lubricant selected from the group consisting of magnesium stearate, sodium stearate, powdered stearic acid, talc, paraffin, cocoa butter, graphite, lycopodium or combinations thereof.

16. A controlled release bolus for administering supplemental magnesium to ruminants over an extended period, comprising:
   from about 50 to about 95 weight percent of olivine;
   from about 1 to about 50 weight percent of urea; and
   from about 0.5 to about 10 weight percent of a binder.

17. The bolus of claim 16, wherein said binder is selected from the group consisting of sodium bentonite, ethyl cellulose, stearic acid, calcium stearate, adipic acid, fumaric acid, polyethylene glycol, deacetylated chitlon and cellulose acetate.

18. The bolus of claim 16, additionally containing a lubricant selected from the group consisting of magnesium stearate, sodium stearate, powdered stearic acid, talc, paraffin, cocoa butter, graphite, lycopodium or combinations thereof.

* * * * *

UNITED STATES PATENT AND TRADEMARK OFFICE
CERTIFICATE OF CORRECTION

PATENT NO. : 4,670,248

DATED : June 2, 1987

INVENTOR(S) : Brian R. Schricker

It is certified that error appears in the above-identified patent and that said Letters Patent are hereby corrected as shown below:

In the Abstract, line 7, "hypomaganesemia" should read -- hypomagnesemia --

Column 1, line 53, "hypomaganesemia" should read -- hypomagnesemia --

Column 1, line 62, "hypomaganesemia" should read -- hypomagnesemia --

Column 1, lines 62 and 63, "Hypomaganesemia" should read -- Hypomagnesemia --

Column 1, line 66, "caustive" should read -- causative --

Column 2, line 25, "magneisum" should read -- magnesium --

Column 2, line 65, "fumaric cid" should read -- fumaric acid --

Column 3, line 41, "monensn" should read -- monensin --

Column 3, line 52, "oxytetra-cyline" should read -- oxytetra-cycline --

Column 4, line 2, "injestion" should read -- ingestion --

Column 4, line 13, "logdement" should read -- lodgement --

Column 5, line 41, "magensium" should read -- magnesium --

Column 5, line 46, "effectly" should read -- effectively --

Claim 1, line 13, "buiret" should read -- biuret --

Claim 7, line 7, "ezymes" should read -- enzymes --

Claim 10, line 3, "acetbutdylate" should read -- acetbutylate --

Claim 11, line 3, "oxytetra-cyline" should read -- oxytetra-cycline --

UNITED STATES PATENT AND TRADEMARK OFFICE
CERTIFICATE OF CORRECTION

PATENT NO. : 4,670,248

DATED : June 2, 1987

INVENTOR(S) : Brian R. Schricker

It is certified that error appears in the above-identified patent and that said Letters Patent is hereby corrected as shown below:

Claim 12, line 3, "monensn" should read -- monensin --.

Signed and Sealed this

Seventh Day of June, 1988

Attest:

DONALD J. QUIGG

Attesting Officer

Commissioner of Patents and Trademarks